(12) United States Patent
Dhanoa

(10) Patent No.: US 8,557,994 B2
(45) Date of Patent: Oct. 15, 2013

(54) DEUTERIUM-ENRICHED PYRIDINONECARBOXAMIDES AND DERIVATIVES

(76) Inventor: Daljit Singh Dhanoa, Del Mar, CA (US)

( * ) Notice: Subject to any disclaimer, the term of this patent is extended or adjusted under 35 U.S.C. 154(b) by 218 days.

(21) Appl. No.: 12/804,621

(22) Filed: Jul. 26, 2010

(65) Prior Publication Data

US 2011/0021557 A1    Jan. 27, 2011

Related U.S. Application Data

(60) Provisional application No. 61/271,720, filed on Jul. 27, 2009.

(51) Int. Cl.
*C07D 513/04*    (2006.01)
*A61K 31/4365*    (2006.01)

(52) U.S. Cl.
USPC .......................... 546/113; 514/301

(58) Field of Classification Search
USPC .......................... 546/113; 514/301
See application file for complete search history.

(56) References Cited

U.S. PATENT DOCUMENTS 6,221,335 B1*    4/2001    Foster ........................ 424/1.81
2005/0256153 A1*    11/2005    Dhanoa et al. ............... 514/301

OTHER PUBLICATIONS

Kushner et al., "Pharmacological uses and perspectives of heavy water and deuterated compounds" Canadian Journal of Physiology and Pharmacology, 1999, 77, 79-88.*
Dyck et. al., Journal of Neurochemistry 1986, 46, 399-404.*

* cited by examiner

*Primary Examiner* — David K O Dell
(74) *Attorney, Agent, or Firm* — Karl Neidert

(57) ABSTRACT

The present invention relates to deuterium-enriched pyridinone carboxamides and their derivatives of the formula I, and pharmaceutically acceptable salts thereof,

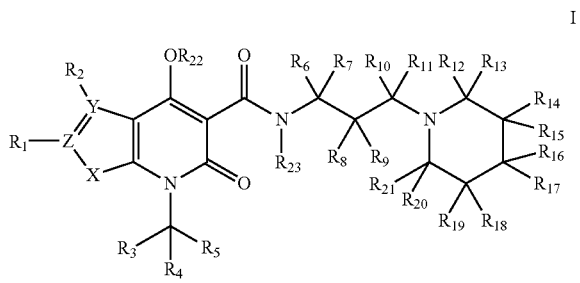

are partial or full agonists of serotonin (5-Hydroxytryptamine or 5-HT$_4$) receptor subtype 4, and are useful compounds for the prevention and treatment of Alzheimer's disease, cognitive and memory dysfunction, mild cognition impairment, memory decline, cognitive impairment associated with schizophrenia, cognitive impairment associated with age-related dementia or Alzheimer's disease, cognitive impairment associated with post-coronary bypass surgery, attention deficit hyperactivity disorder, speech improvement in autistic children, sleep apnea in Alzheimer's patients, irritable bowel syndrome, gastroesophageal reflux disease, Crobn's disease, emesis, nausea, vomiting, prokinesia, non-ulcer dyspepcia, anxiety, depression, pain, migraine, urinary incontinence, arterial fibrillation, arrhythmia, ischemic stroke, gastric emptying disorders, gastritis, gastrointestinal disorders, feeding disorders, obesity, anorexia, constipation, respiratory depression, and erectile dysfunction.

5 Claims, No Drawings

DEUTERIUM-ENRICHED PYRIDINONECARBOXAMIDES AND DERIVATIVES

CROSS-REFERENCE TO RELATED APPLICATIONS

The present application claims priority benefit under 35 U.S.C. article section 119(e) of U.S. Provisional Patent Application Ser. No. U.S. 61/271,720 filed 27 Jul. 2009. The disclosure of this application is incorporated herein by reference.

SUMMARY OF THE INVENTION

The present invention is concerned with deuterium-enriched pyridinone carboxamides and derivatives thereof of formula I,

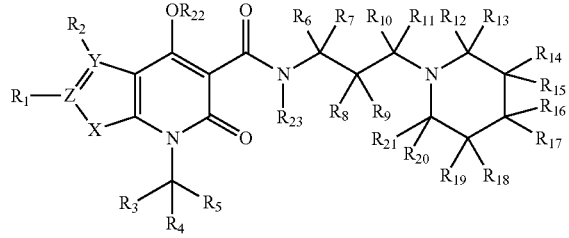

Wherein, $R_1$ and $R_2$ are independently, H, D (deuterium with enrichment of 1%-100%), F, Cl, $CD_3$ (methyl-$d_3$), $CH_2CD_3$, $CD_2CD_3$, $CH_2CH_2CD_3$, OD, $OCD_3$;

$R_3$, $R_4$ and $R_5$ are independently H, D (Deuterium with 1%-100%), $CD_3$, cyclopropyl-d (c-Pr-$d_1$-$d_5$), $R_3$ joined with $R_4$ or $R_5$ to form cyclopropane ring;

$R_6$, $R_7$, $R_8$, $R_9$, $R_{10}$ and $R_{11}$ are independently, H, D (Deuterium with 1%-100% enrichment);

$R_{12}$, $R_{13}$, $R_{14}$, $R_{15}$, $R_{16}$, $R_{17}$, $R_{18}$, $R_{19}$, $R_{20}$, and $R_{21}$ are independently H, D (Deuterium with 1%-100% enrichment incorporated), F, Cl, $CH_3$, $CD_3$, $CF_3$, $CH_2CH_3$, $CD_2CD_3$, $CH_2CF_3$, $CF_2CF_3$, $CH_2CH_2CH_3$, $CD_2CD_2CD_3$, OH, $OCH_3$, $OCD_3$, $OCF_3$, CN; $CO_2CH_3$, $CO_2CD_3$, OH, OD, $OCF_3$, $OCD_3$, $NO_2$, $SO_2R$(R is C1-C3 alkyl, C1-C6 cycloalkyl);

$R_{22}$ is H, D (deuterium), $CD_3$;

$R_{23}$ is H, D, $CD_3$;

X, Y and Z are independently, S, N, C, O, and C=C.

The compounds of formula I and acceptable pharmaceutical salts thereof are 5-$HT_4$ receptor agonists (partial or full agonists) and are useful for the prevention and treatment of Alzheimer's disease, cognitive and memory dysfunction, mild cognition impairment, memory decline, cognitive impairment associated with schizophrenia, cognitive impairment associated with age-related dementia or Alzheimer's disease, cognitive impairment associated with post-coronary bypass surgery, attention deficit hyperactivity disorder, speech improvement in autistic children, sleep apnea in Alzheimer's patients, irritable bowel syndrome, gastroesophageal reflux disease, Crohn's disease, emesis, nausea, vomiting, prokinesia, non-ulcer dyspepcia, anxiety, depression, pain, migraine, urinary incontinence, arterial fibrillation, arrhythmia, ischemic stroke, gastric emptying disorders, gastritis, gastrointestinal disorders, feeding disorders, obesity, anorexia, constipation, respiratory depression, and erectile dysfunction.

One of the objectives of the present invention is to provide deuterium enriched compounds of formula I or a pharmaceutically acceptable salt thereof.

It is another objective of the present invention to provide pharmaceutical compositions comprising a pharmaceutically acceptable carrier and a therapeutically effective amount of at least one of the deuterium enriched compounds of the present invention or a pharmaceutically acceptable salt thereof.

It is another object of the present invention to provide a fully (all H atoms replaced with deuterium) or partially (one or more H atoms of a compound replaced with deuterium) deuterated compound of formula I or a pharmaceutically acceptable salt thereof.

It is another object of the present invention to provide a chlorine-substituted ($R_1$=Cl) deuterium-enriched compound derivative of formula I or a pharmaceutically acceptable salt thereof.

It is another object of the present invention to provide a florine-substituted ($R_1$=F) deuterium-enriched compound derivative of formula I or a pharmaceutically acceptable salt thereof.

It is another object of the present invention to provide a method for treating Alzheimer's disease comprising administering to a host in need of such treatment a therapeutically effective amount of at least one of the compounds of the present invention or a pharmaceutically acceptable salt thereof.

It is another object of the present invention to provide a method for treating cognitive impairment and/or cognitive dysfunction comprising administering to a host in need of such treatment a therapeutically effective amount of at least one of the compounds of the present invention or a pharmaceutically acceptable salt thereof.

It is another object of the present invention to provide a method for treating memory impairment, or memory decline or memory dysfunction comprising administering to a host in need of such treatment a therapeutically effective amount of at least one of the compounds of the present invention or a pharmaceutically acceptable salt thereof.

It is another object of the present invention to provide a method for treating memory impairment, or memory decline or memory dysfunction associated with schizophrenia comprising administering to a host in need of such treatment a therapeutically effective amount of at least one of the compounds of the present invention or a pharmaceutically acceptable salt thereof.

It is another objective of the present invention to provide the use of a novel compound of formula I or a pharmaceutically acceptable salt thereof for the manufacture of a medicament for the treatment of Alzheimer's disease and related cognitive and memory dysfunctions, cognitive and memory impairment associated with schizophrenia, and frontotemporal dementias.

It is another object of the present invention to provide a method for treating various disease by compounds of formula I, as a monotherapy or in combination with other cognition and memory enhancing medicaments such as acetylcholine esterase inhibitor, donepezil or a NMDA glutamate receptor blocker, memantine, comprising administering to a host in need of such treatment a therapeutically effective amount of at least one of the compounds of the present invention or a pharmaceutically acceptable salt thereof.

BACKGROUND OF THE INVENTION

Neurotransmitter serotonin or 5-Hydroxytryptamine (5-HT) is abundantly distributed in the central nervous system, including hippocampus and frontal cortex. 5-HT receptors are a family of G-protein coupled receptors, characterized with 7-transmembrane helices and presently have fourteen known receptor subtypes, some of which exist as multiple splice variants [D. L. Murphy, A. M. Andrews, C. H. Wichems, Q. Li, M. Tohda and B. Greenberg, *J. Clin. Psychiatry,* 1998, 59 (suppl. 15), 4]. 5-HT influences a number of physiological functions and is implicated in a large number of central nervous system disorders and neurodegenerative diseases [W. E. Childers, Jr. and A. J. Robichaud, *Ann. Rep. Med. Chem.* 2005, 40, 17].

The 5-HT$_4$ receptors are a member of the superfamily of G-protein coupled receptors with seven transmembrane (7TM) domains coupled to a G-protein which is positively coupled to adenylate cyclase. The 5-HT$_4$ receptors are expressed in a wide variety of tissues, including the human brain and the rodent brain, and human, dog, pig and rodent gastro-intestinal tract, and the pig and human heart. In the human brain, the presence of 5-HT$_4$ receptors has been shown in basal ganglia and in the caudate putamen nuclei, where the density is the highest [Bonacenture, Hall, Gommersen, Cras, langlois, Jurzak, Leysen, *Synapse,* 2000, 36, 35]. In the mammalian brain, the 5-HT$_4$ receptors contribute to dopamine secretion and regulate learning and long-term memory via the modification of acetylcholine release. In the central nervous system of guinea-pigs and rats, 5-HT$_4$ receptors are expressed in two anatomical and functional structures: the extrapyramidal motor system and the mesolimbic system [Patel, Roberts, Moorman, Reavill, *Neuroscience,* 1995, 69, 1159; Grossman, Kilpatrik, Bunce, *Br. J. Pharmacol.* 1993, 109, 618].

In the peripheral tissues, the 5-HT$_4$ receptors have proven to regulate gastro-intestinal tract motility, intestinal electrolyte secretion, adrenal secretion of corticosteroids, bladder contraction and atrium contractility. Significant advances have been made in the 5-HT$_4$ receptor studies during the past decade that culminated in the development of 5-HT$_4$ agonists and partial agonists, e.g. Tegaserod, for the treatment of irritable bowel syndrome [Giger, Mattes, Pfannkuche, *Ann. Rep Med. Chem.* 2007, 42, 195].

The 5-HT$_4$ receptors are involved in a wide variety of central and peripheral disorders, including neurodegenerative disorders such as Alzheimer's disease, cognition disorders, irritable bowel syndrome, nausea, emesis, vomiting, prokinesia, gastroesophageal reflux disease, nonulcer dyspepsia, depression, anxiety, urinary incontinence, migraine, arrhthymia, atrial fibrillation, ischemic stroke, gastritis, gastric emptying disorders, feeding disorders, gastrointestinal disorders, constipation, erectile dysfunction, and respiratory depression.

The role of the 5-HT$_4$ receptor has been implicated in the pathology of Alzheimer's disease and related cognitive function [J. Bockaert, S. Claeyseen, V. Compan and A. Dumuis. *Curr. Drug. Targets: CNS & Neurolog. Disorders,* 2004, 3, 39; P. C. Moser, O. E. Bergis, S. Jegham, A. Lochead, E. Duconseille, T. Elee, J.-P. Terranova, D. Caille, I. Berque-Bestel, F. Lezoualch, R. Fischmeister, A. Dumuis, J. Bockaert, G. Pascal, P. Soubrie and B. Scatton, *J. Pharmacol. Exp. Ther.* 2002, 302, 731]. A recent report provides evidence from transgenic animal studies that supports the finding that the 5-HT$_4$ receptor is a novel target for cognitive enhancement and that only a partial agonist is needed for producing the beneficial effect in increasing cognition function. Moreover, the 5-HT$_4$ receptor remains functional even in the presence of excess of A□ □ for Alzheimer's drug discovery [J. P. Spencer, J. T. Brown, J. C. Richardson, A. D. Medhurst, S. S. Sehmi, A. R. Calver, A. D. Randall, Neuroscience, 2004, 129, 49]. Stimulation of the 5-HT$_4$ receptor promotes an increase in the production and release of acetylcholine (ACh) in the brain unlike the cholinesterase inhibitors that prevent degradation of ACh for symptomatic improvement in Alzheimer's disease patients. The activation of 5-HT4 receptor also leads to secretion of the soluble form of amyloid precursor protein (sAPPα), and decrease in Aβ levels via promoting the a-secretase pathway [M. Cachard,-Chastel, F. Lezoualc'h, I. Dewachter, C. Delomenie, S. Croes, H. Devijver, M. Langlois, F. V. Leuven, S. Sicsic, and A. M. Gardier. *Brit. J. Pharmacol.* 2007, 150, 883]. Evidence in vivo rat studies of the role of activation of 5-HT4 receptor in the production of sAPPαhas recently been reported [S. Cho and Y. Hu, Exper. *Neurology,* 2007, 203, 274]. The protein, sAPPα is neuroprotective, enhances memory, increases NGF and competes with amyloidogenic (insoluble) APP peptides. Considering the significant evidence reported, it is evident that 5-HT$_4$ receptor agonists may have potential not only in the treatment of Alzheimer's disease but also modification of the disease by slowing and inhibiting its progression [F. Lezoualc'h, *Exper. Neurology,* 2007, 205, 325].

The novel compounds of formula I have 5-HT$_4$ partial agonist activity and/or full agonist activity, inverse agonist activity and antagonist activity and have applications as safer and effective therapeutic drugs for the treatment of Alzheimer's disease and age-related cognitive and memory dysfunction and cognitive and memory impairment associated with schizophrenia. These compounds may also have applications in the treatment of gastrointestinal disorders including irritable bowel syndrome, Crohn's disease, gastroesophageal reflux disease, emesis, nausea, vomiting, prokinesia, non-ulcer dyspepcia, anxiety, depression, pain, migraine, urinary incontinence, arterial fibrillation, arrhythmia, ischemic stroke, gastric emptying disorders, gastritis, gastrointestinal disorders, feeding disorders, obesity, anorexia, constipation, constipation, respiratory depression, and erectile dysfunction.

DETAILED DESCRIPTION OF THE INVENTION

The present invention relates to compounds of formula 1, their pharmaceutically acceptable salts, compositions and uses thereof as 5-HT$_4$ partial agonists, or 5-HT$_4$ full agonists, 5-HT$_4$ inverse agonists, 5-HT$_4$ antagonists, as mono therapy for treating, preventing or curing Alzheimer's disease, memory conditions, cognition disorders, and depression, or in combination with existing therapies.

Deuterium (D or $^2$H) is a stable isotope non-radioactive isotope of hydrogen (H) and has an atomic weight of 2.0144. Hydrogen occurs naturally as a mixture of the isotopes $^1$H, D ($^2$H), and T ($^3$H or tritium) and the natural abundance of deuterium is 0-015%. One of ordinary skill in the art recognizes that in all compounds containing H atom, H actually represents a mixture of H and D, with about 0-015% of D. So, compounds with a level of D that has been enriched to be greater than its natural abundance of 0.015%, should be considered unnatural and as a result novel as compared to their corresponding non-enriched counterparts.

The carbon-hydrogen bonds contain a naturally occurring distribution of hydrogen isotopes, namely $^1$H or protium (about 99.9844%), $^2$H or deuterium (D) (about 0.0156%), and $^3$H or tritium (in the range between about 0.5 and 67 tritium atoms per $10^{18}$ protium atoms). Higher levels of deuterium incorporation produce a detectable Kinetic Isotope Effect (Werstiuk, N. H.; Dhanoa, D. S.; Timmins, G. Can J. Chem. 1979, 57, 2885; Werstiuk, N. H.; Dhanoa, D. S.; Timmins, G. Can J. Chem. 1983, 61, 2403), that could improve the pharmacokinetic, pharmacologic and/or toxicologic parameters of compounds of formula I in comparison to compounds having naturally occurring levels of deuterium and their corresponding hydrogen (protium) analogs. The present invention disclosed herein describes novel compounds of formula I containing higher content of deuterium (>1%), synthesis and uses thereof as 5-HT$_4$ partial agonists and/or full agonists and inverse agonist and antagonists for the treatment of central nervous system diseases including Alzheimer's disease, Parkinson's disease, anxiety, depression, schizophrenia, insomnia, nausea, emesis, epilepsy, pain and others. Suitable modifications of certain carbon-hydrogen bonds into carbon-deuterium bonds may generate novel substituted pyridinone carboxamides with unexpected and non-obvious improvements of pharmacological, pharmacokinetic and toxicological properties in comparison to the non-isotopically enriched 5-HT$_4$ agonist, full agonists, inverse agonists or antagonists. This invention relies on the judicious and successful application of chemical kinetics to drug design. Deuterium incorporation levels in the compounds of the invention are significantly higher than the naturally-occurring levels and are sufficient to induce at least one substantial improvement as described herein. All percentages given for the amount of deuterium (D or d) present are mole percentages.

Deuterium enrichment" refers to the percentage of incorporation of deuterium at a given site on the molecule instead of a hydrogen atom. For example, deuterium enrichment of 1% means that in 1% of molecules in a given sample a particular site is occupied by deuterium. Because the naturally occurring distribution of deuterium is about 0.0156%, deuterium enrichment in compounds synthesized using non-enriched starting materials is about 0.0156%.

It can be a significant synthetic challenge to produce 100% deuterium at a specific site of a compound. When 100% deuteration is recited or a deuterium atom is specifically shown in a chemical structure of a compound, a small amount of deuterium may still be present. Higher levels of deuterium content in a compound can be produced either by Hydrogen-Deuterium (H-D) exchange or by synthesizing the compound for specific deuteration. The H-D exchange is readily achieved in case of H atoms attached to heteroatoms for example in cases of carboxylic acids (COOH), sulfonamides (SO$_2$NH$_2$), alcohols (OH), basic amines (NH$_2$), etc. However, these incorporated D attached to hetero atoms (O, N, S) etc, readily revert back to H upon exposure to water or any acidic compounds containing H atoms. The preferred deuterium containing compounds are the ones which contain D directly attached to carbon atoms of the structure of the compounds of this invention.

In some embodiments, the deuterium enrichment in the compounds of the present invention is greater than 4%, 5%, 6%, 7%, 8%, 9% or 10%. In other embodiments, the deuterium enrichment in the compounds of the present invention is greater than 20%. In further embodiments, the deuterium enrichment in the compounds of the present invention is greater than 50%. In some embodiments, the deuterium enrichment in the compounds of the present invention is greater than 70%. In some embodiments, the deuterium enrichment in the compounds of the present invention is greater than 90%.

This invention is concerned with deuterium-enriched compounds of structural formula I,

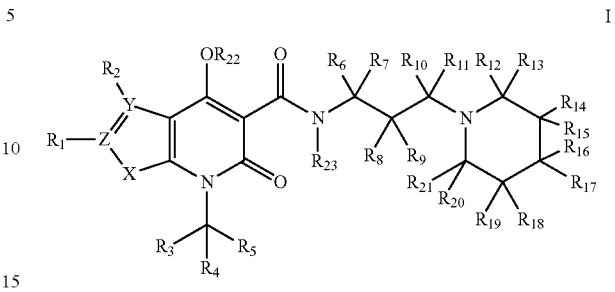

or a pharmaceutically acceptable salt thereof, wherein,
$R_1$ and $R_2$ are independently, H, D (deuterium with enrichment of 1%-100%), F, Cl, CD$_3$ (methyl-d$_3$), CH$_2$CD$_3$, CD$_2$CD$_3$, CH$_2$CH$_2$CD3, OD, OCD$_3$;
$R_3$, $R_4$ and $R_5$ are independently H, D (Deuterium with 1%-100%), CD$_3$, cyclopropyl-d (c-Pr-d$_1$-d$_5$), $R_3$ joined with $R_4$ or $R_5$ to form cyclopropane ring;
$R_6$, $R_7$, $R_8$, $R_9$, $R_{10}$ and $R_{11}$ are independently, H, D (Deuterium with 1%-100% enrichment);
$R_{12}$, $R_{13}$, $R_{14}$, $R_{15}$, $R_{16}$, $^{R17}$, $R_{18}$, $R_{19}$, $R_{20}$, and $R_{21}$ are independently H, D (Deuterium with 1%-100% enrichment incorporated), F, Cl, CH$_3$, CD$_3$, CF$_3$, CH$_2$CH$_3$, CD$_2$CD$_3$, CH$_2$CF$_3$, CF$_2$CF$_3$, CH$_2$CH$_2$CH$_3$, CD$_2$CD$_2$CD$_3$, OH, OCH$_3$, OCD$_3$, OCF$_3$, CN; CO$_2$CH$_3$, CO$_2$CD$_3$, OH, OD, OCF$_3$, OCD$_3$, NO$_2$, SO$_2$R (R is C1-C3 alkyl, C1-C6 cycloalkyl);
$R_{22}$ is H, D (deuterium), CD$_3$;
$R_{23}$ is H, D, CD$_3$;
X, Y and Z are independently, S, N, C, O, and C=C.
Pharmaceutically acceptable salts selected from the group consisting of potassium, sodium, calcium, magnesium, lithium, hydrochloride, acetate, acetate, trifluoroacetate, mesylate, maleate, brosylate, fumarate, citrate, tartarate, salts;
A pharmaceutical composition comprising the compound of formula I and a pharmaceutically acceptable carrier.

DEFINITIONS

The examples provided in the definitions present in this application are non-inclusive unless otherwise stated. They include but are not limited to recited examples. The compounds of the present may have various isomers including all streoisomers of asymmetric atoms and geometric, tautomeric or rotamers, and all isomers are considered to be part of the present invention. All processes used to prepare compounds of the present invention and intermediates made therein are considered to be part of the present invention.

"Pharmaceutically acceptable salts" refer to derivatives of the disclosed compounds wherein the parent compound is modified by making acid or base salts thereof. Examples of the pharmaceutically acceptable salts include, but not limited to, mineral or organic acid salts of the basic residues. The pharmaceutically acceptable salts include but not limited to potassium, sodium, calcium, magnesium, lithium, HCl, HBr, HI, acetic, trifluoroacetic, citric, ascorbic, benzoin, methanesulfonic, benzenesulfonic, bicarbonic, carbonic, ethane disulfonic, edetic, fumaric, maleic, lactic, malic, mandelic, gluconic, glutamic, glycolic, glycollyarsanilic, lauryl, hexylresorcinic, hyrdabamic, hydroxymaleic, hydroxynaphthoic, isethionic, lactobionic, napsylic, nitric, oxalic, pamoic, pantothenic, phenyllacetic, phosphoric, polygalacturonic, propionic, salicyclic, stearic, subacetic, succinic, sulfamic, sulfanilic, sulfuric, tannic, tartaric, tolouenesulfonic, and p-bromobenzenesulfonic.

General Methods for Preparation of Deuterium-Enriched Compounds of Formula I

The deuterium-enriched compounds of formula I are prepared as described in Scheme 1 and 2. The compounds containing deuterium at the heteroatoms, oxygen and nitrogen are prepared by treating precursor (e.g. OH, or CONH, $SO_2NH$) with deuterium oxide or deuterated acetic acid-$d_1$ or $d_4$ ($CH_3OD$ or $CD_3OD$). The incorporation of deuterium (directly attached to carbon atom of the compound) into the chemical structure of the compound is achieved by using various synthetic chemical methods as described below or extension of the methods available.

(1) Reductive amination between a carbonyl group and an appropriate amine using a deuterated reducing agent e.g. triacetoxy sodium borohydride ($NaBH(OAc)_3$ or sodium tetradeuteride, lithium aluminum deuteride or sodium cyanodeuteride and other nucleophilic deuteride (hydride) agents available commercially or in the literature.

(ii) Electrophilic addition or aromatic substitution of unsaturated C=C double bonds or aromatic or heteroaromatic ring system (iii) Deuterium atom exchange for H atom of an aromatic ring system under high reaction temperature conditions.

(v) Hydrogen-Deuterium (H-D) exchange of H atoms bonded to heteroatoms, O, N, COOH, $SO_2NH$ etc.

The general synthetic methods used for the preparation of compounds of this invention are described in Scheme 1 and Scheme 2.

The key intermediates, are 4, 5, prepared from the appropriately designed deuterated aldehyde 1, using steps A and B.

Step A:

To a solution of acetaldehyde-$d_4$ 1 in toluene is added 1.2 equivalent of ethyl cyanoacetate 2 (2.2 g) and ammonium acetate followed by acetic acid. The mixture is refluxed for 12 h under nitrogen using Dean-Stark apparatus. After cooling to room temperature by allowing it to stand, the reaction mixture is concentrated using rotary evaporator under vacuum to remove solvent. To the concentrated residue, was added water and the adduct product 3 is extracted with ethyl acetate. The combined organic layer is dried over anhydrous sodium sulfate or anhydrous magnesium sulfate and concentrated under vacuum. The resulting product 3 obtained as such is used for the next step.

Step B.

Morpholine is added to 3 (12.4 g) in ethanol (15 mL) followed by addition of sulfur in slight excess under nitrogen atmosphere and the suspension is reflux with stirring for 12 h. After cooling to room temperature, the reaction mixture is concentrated in vacuum and the product 4 is extracted with ethyl acetate from acqueous phase. The combined organic layer was dried over anhydrous sodium sulfate, filtered and the filtrate is concentrated in vacuum. Ethyl 2-Aminothiophene-3-carboxylate 4 was purified by column chromatography using mixture of ethyl acetate and hexane.

Step C:

The Ethyl 2-amino thiocarboxylate 4 is converted to the N-alkylated analog by reductive amination of 4 with hexadeutero acetone in the presence of acetic acid in dichloromethane using sodium triacetoxy borodeuteride as illustrated in Scheme 1 above. The compound 4 is mixed with acetone-$d_6$ in methylene chloride and the mixture is stirred with acetic acid. The reducing agent sodium triacetoxy borohydride-$d_1$ is added to the mixture and the resulting mixture stirred until the reaction is completed as monitored by thin layer chromatography. The N-isopropyl-$d_1$ alkylated product 5 is purified by flash column chromatography using ethyl acetate hexane as the eluting solvent mixture.

Step D:

The intermediate 7, another penultimate fragment of the active compounds of this invention is produced by reductive amination of the appropriate piperidine 6 (fully deuterated or partially deuterated piperidine or substituted 4-methyl-piperidine, etc.) with either sodium triacetoxyborohydride or sodium triacetoxyborodeuteride-$d_1$ (or sodium triacetoxyborohydride) with the appropriately selected N-protected propanal (N-protected propanaldehyde).

The alkylated piperidne intermediate 7 is also produced by alkylating piperidine with N-phthalidomido-propyl bromide or N-Boc-propyl bromide or N-CBz propylbromide by refluxing the reaction mixture in toluene.

Step E:

The alkylated piperidine 8 is obtained by deprotection of the intermediate 7. The N-protecting group of 7 is removed by treating it with a suitable reagent e.g. hydrazine in ethanol for removal of phthalidomido group, trifluoroacetic acid for removal of Boc and catalytic hydrogenation for the removal of CBz group.

Step F:

The ethyl aminoester intermediate 5 is converted to the cyclic anhydride intermediate 9 via saponification to the corresponding acid followed by its treatment with triphiosgene.

Step G:

The interemediate 9 produces the pivotal intermediate ethyl β-hydroxypiperidone carboxylate 10 upon treatment with ethyl malonate in the presence of NaH (sodium hydride) in N,N-Dimethylformamide.

Steps A through G are utilized to produce the various compounds of formula I in which the thiophene unit of 10 is varied to the corresponding deuteated or undeuterated regionisomeric thiophenes, thiazoles, oxazoles, pyrazoles, triazoles and benzene derivatives.

Step H:

The ethyl pyridinone carboxylate 10 is refluxed with 3-aminopropyl-1-piperidine 8 in toluene to produce the corresponding desired coupled product, pyridinonecarboxamide 11.

Step I:

The pyridinonecarboxamide 11 is then converted to the corresponding N-deuterated carboxamide by treating with deuterated methanol ($CD_3OD$-$d_4$), which then is converted into the desired salt form upon its treatment with an appropriate base or acid. The pyridinonecarboxamide 11 is transformed into the salt form 12, a compound of formula I, by treating with potassium t-butoxide to yield its potassium salt, or sodium methoxide to give its sodium salt. 11 is treated with hydrochloric acid in ether to produce its HCl salt.

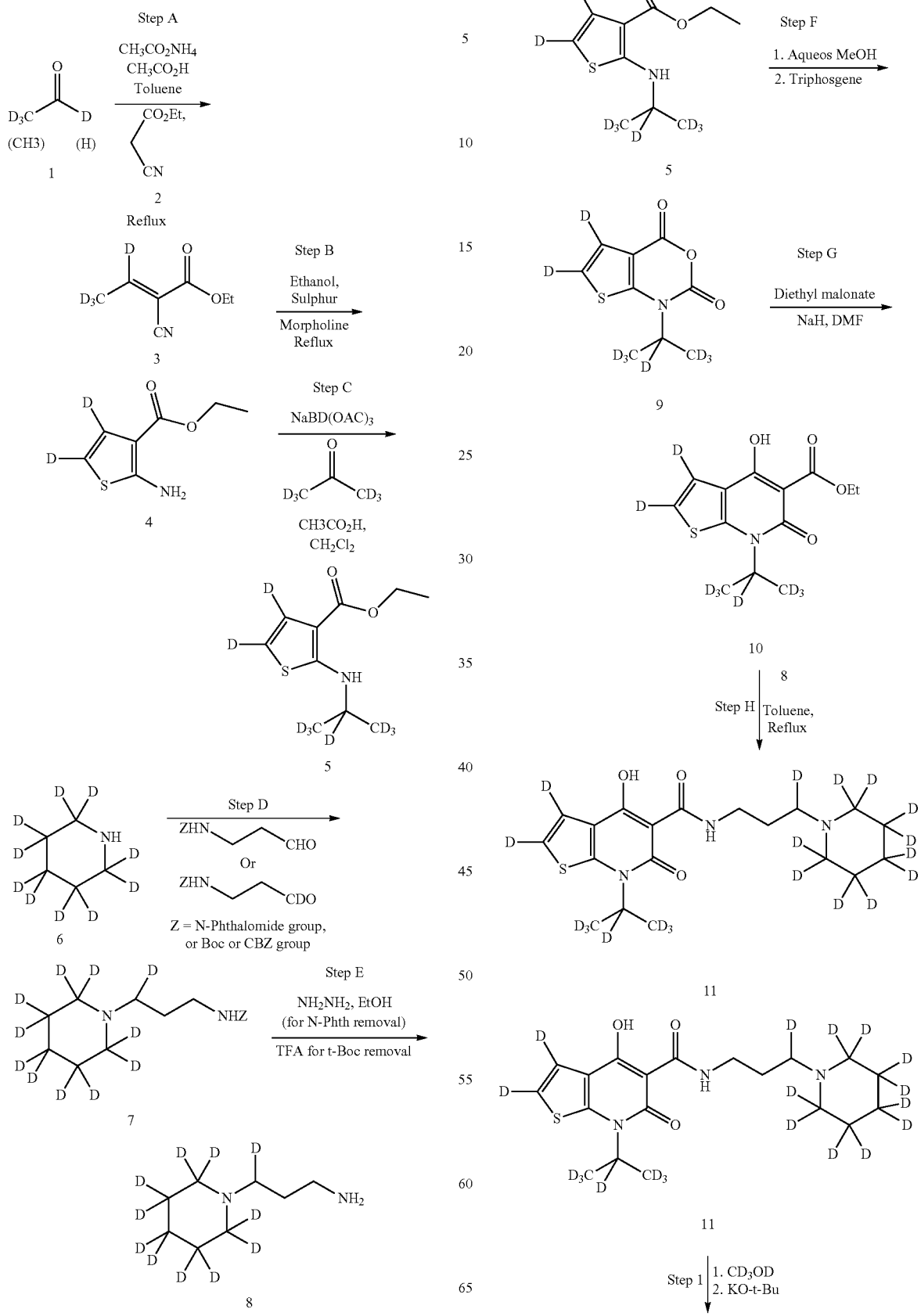

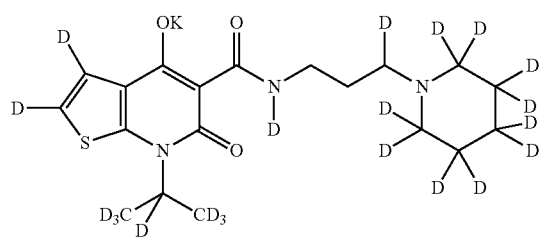

12

Step J:

The regioisomeric aminothiophene carboxylate 15 of the corresponding compound 4 is produced from the treatment of carbonyl compound 13 with phosphien oxychloride (POCl₃) in DMF and hydroxylamine to give 2-chloroacrylonitrile 14 as shown below in Scheme 2.

Step K:

Treatment of 14 with thioglycolic acid in methanol with sodium methoxide produces the target ethyl aminothiophene carboxylate 15 as shown below in Scheme 2.

Various compounds of formula I containing 15 as one of the key fragments are produced by utilizing the step C through step I as given above for Scheme 1.

SCHEME 2:

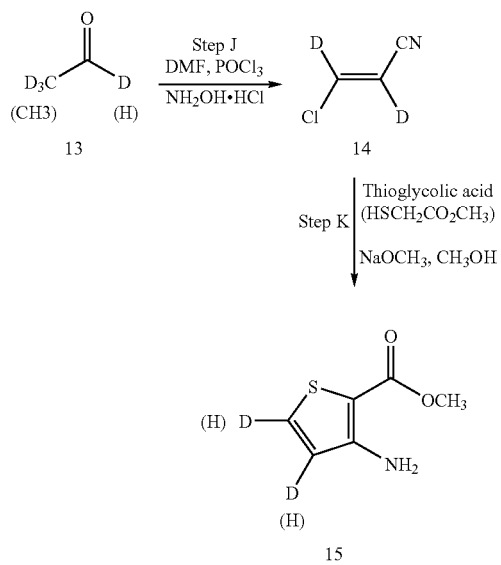

Similarly, using Steps A through Step I are utilized to produce various other compounds of formula I containing 2-halothiophenes, thizole, oxazole, triazole or pyrazole, starting from the corresponding 2-amino-3-carboxylates or 3-amino-2-carboxylate as readily available starting materials.

EXAMPLES

Given below in Table 1 are compounds that are representative examples of the present invention.

TABLE 1

Examples of novel compounds of this invention.

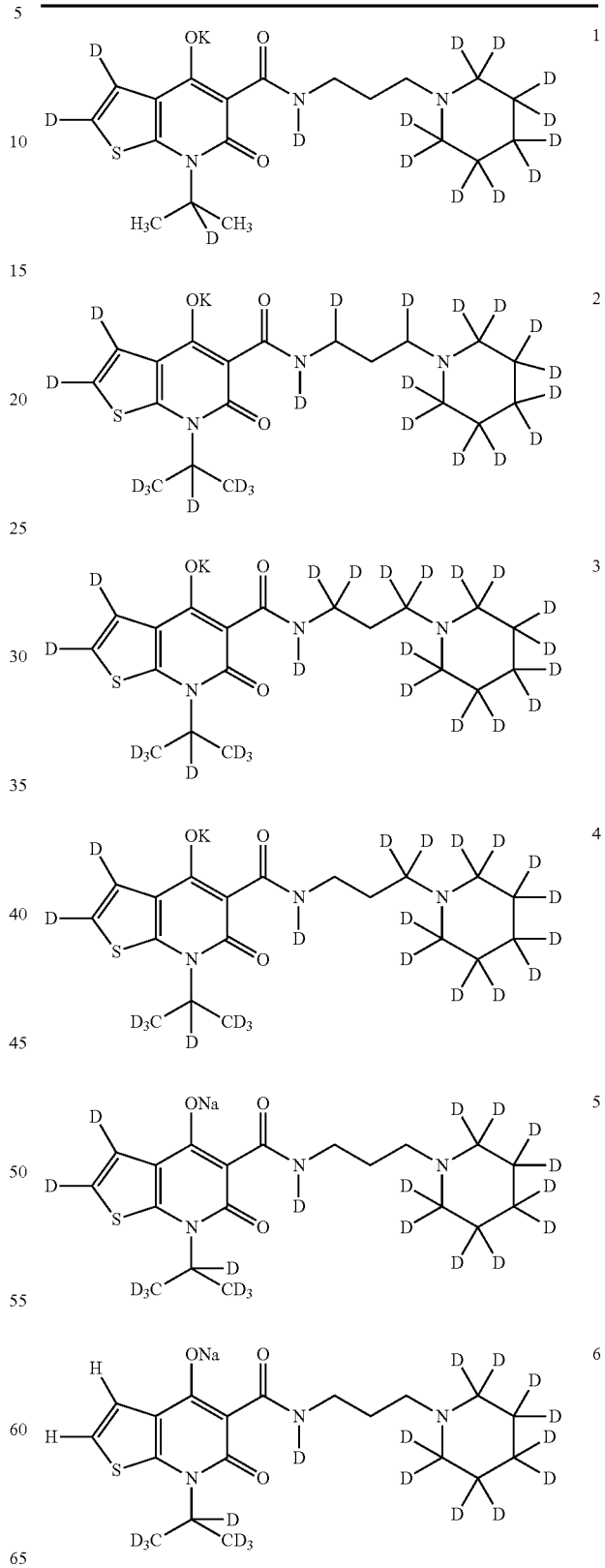

TABLE 1-continued
Examples of novel compounds of this invention.
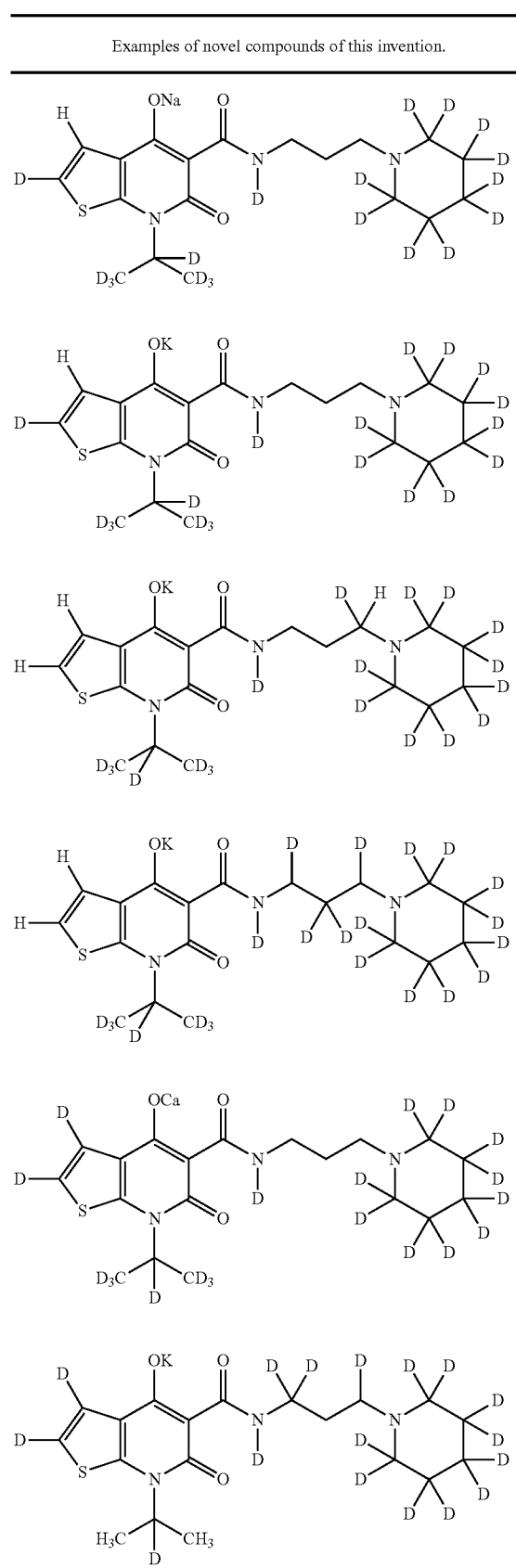
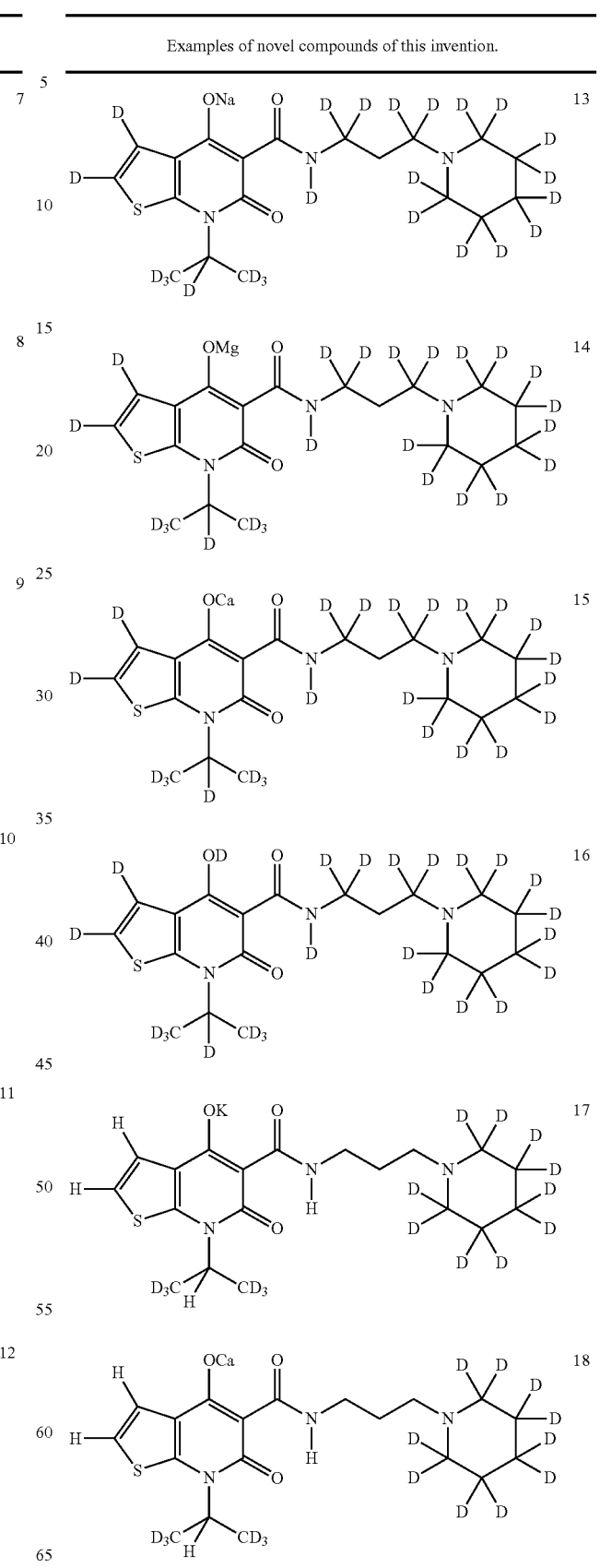

TABLE 1-continued
Examples of novel compounds of this invention.
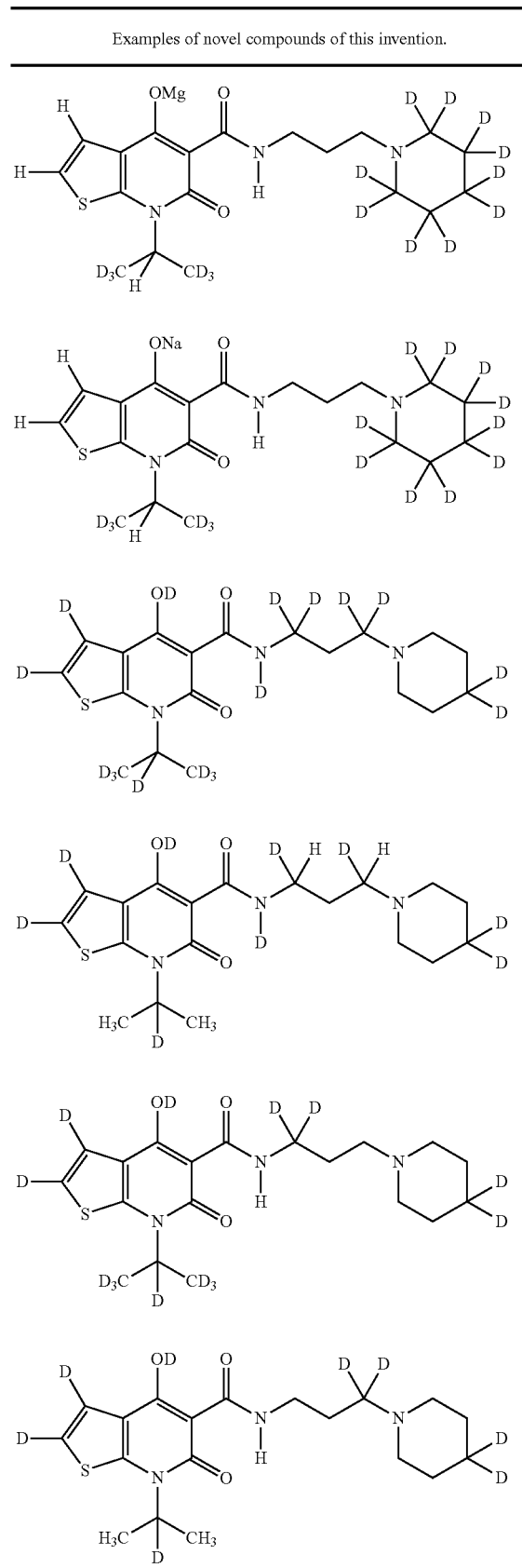
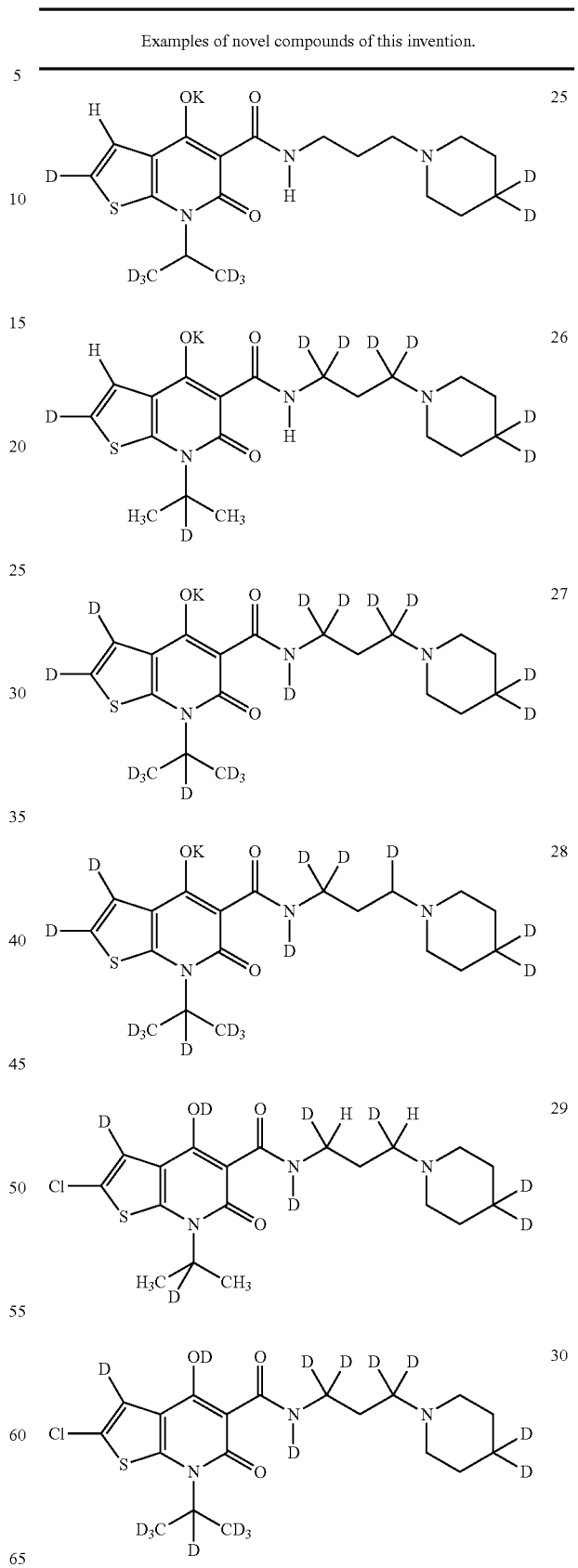

TABLE 1-continued
Examples of novel compounds of this invention.
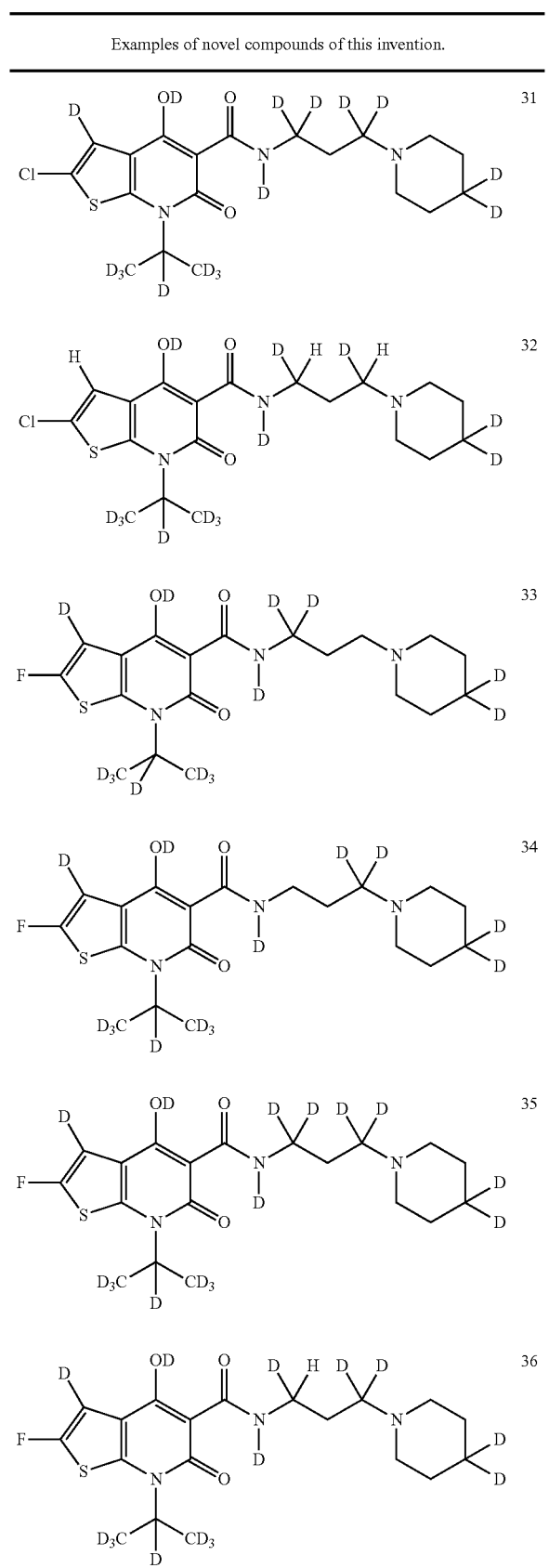
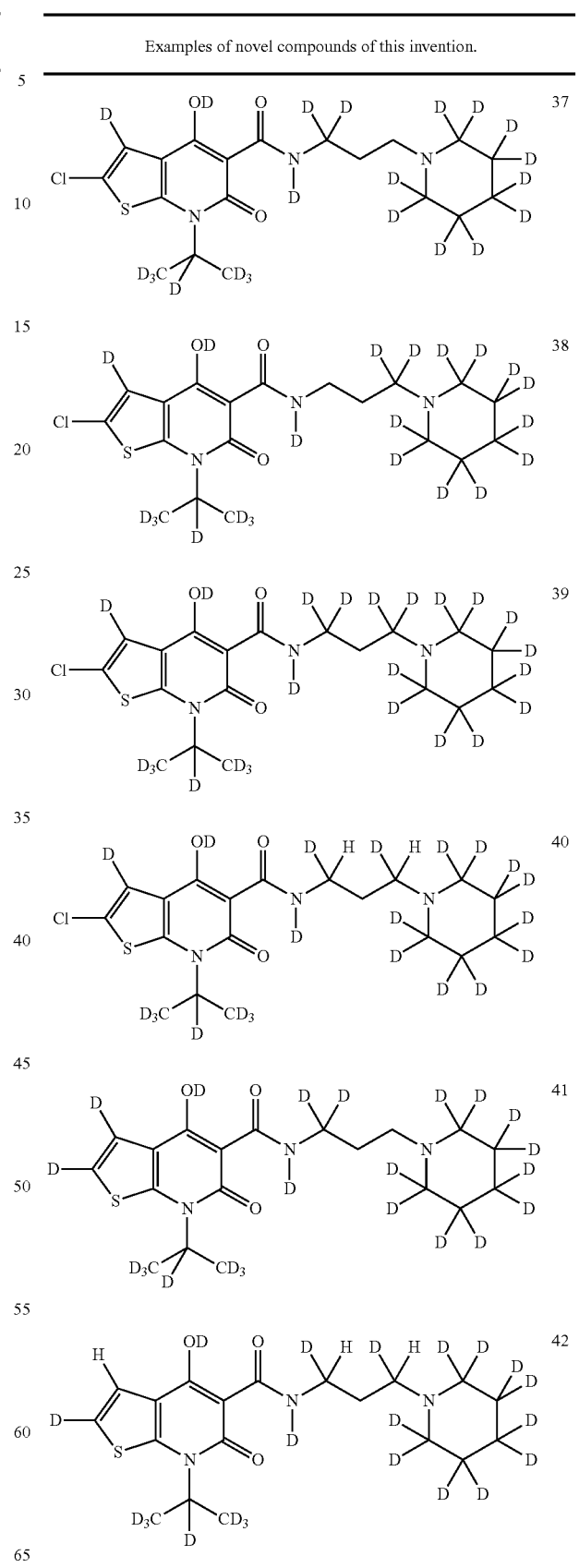

TABLE 1-continued
Examples of novel compounds of this invention.
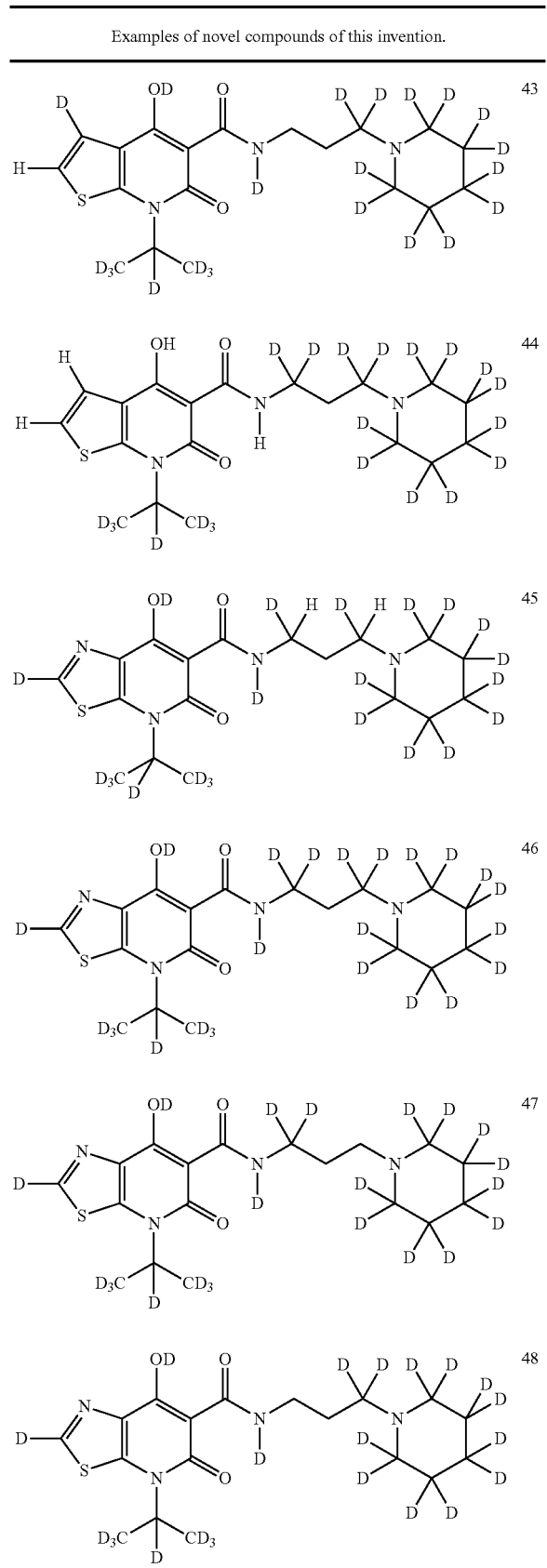
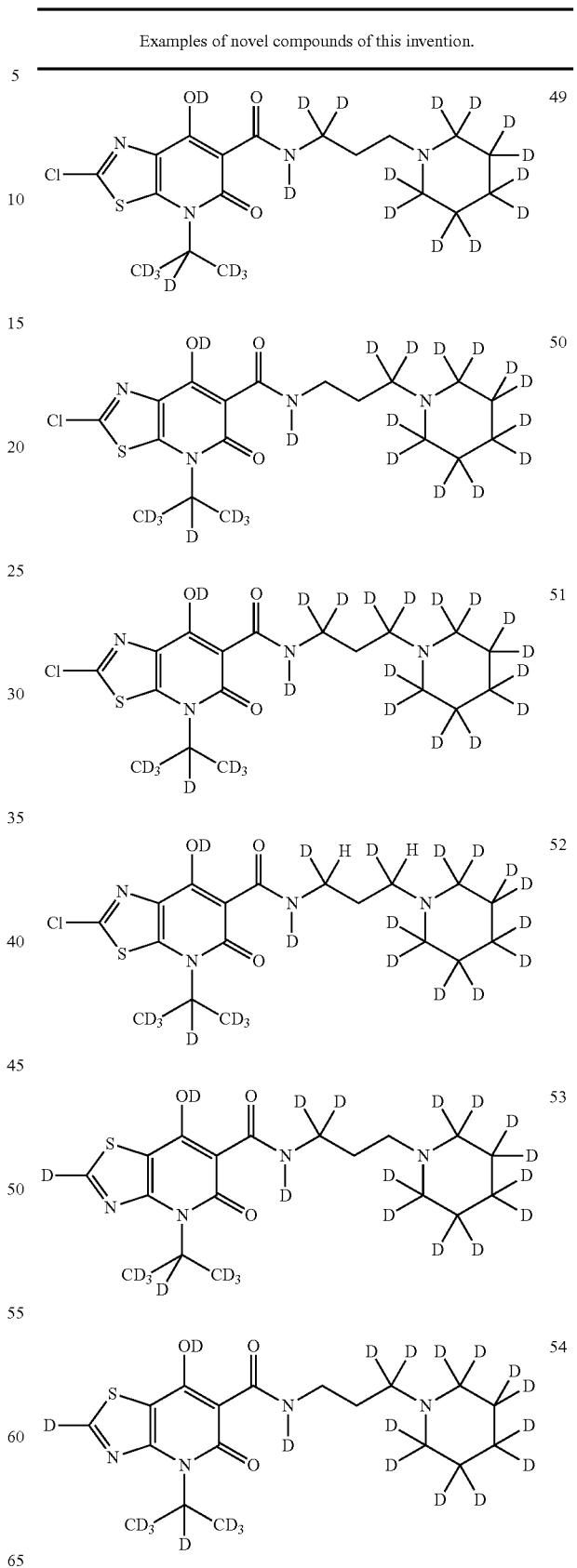

TABLE 1-continued
Examples of novel compounds of this invention.
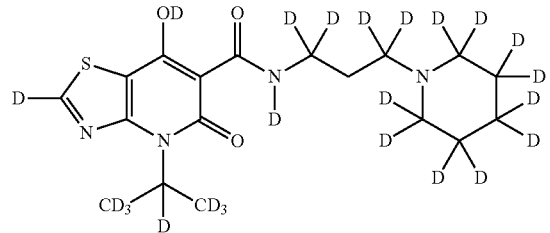
55
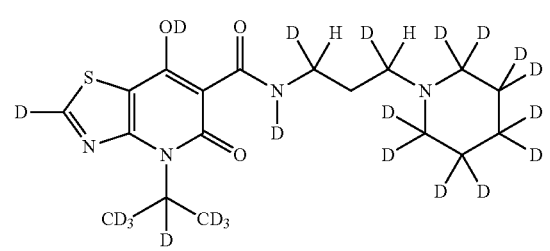
56
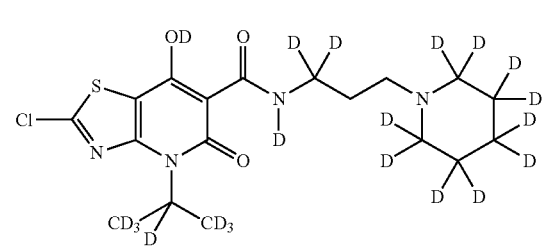
57
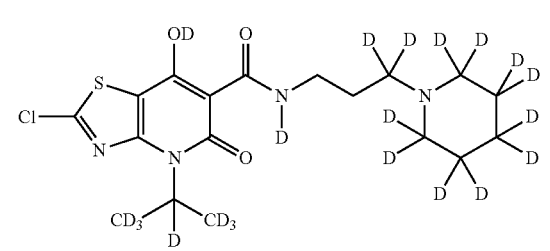
58
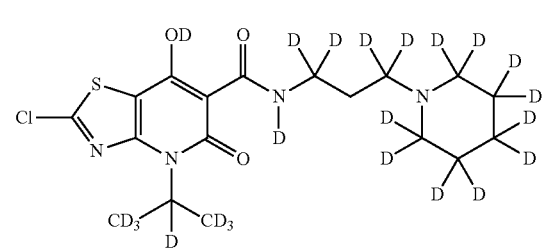
59
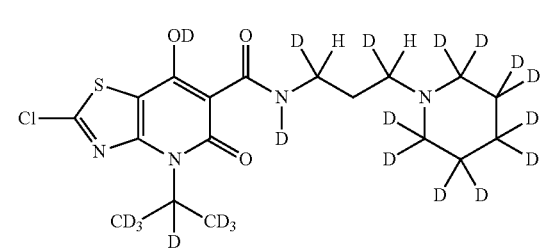
60
TABLE 1-continued
Examples of novel compounds of this invention.
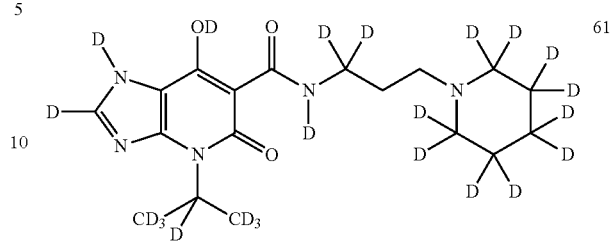
61
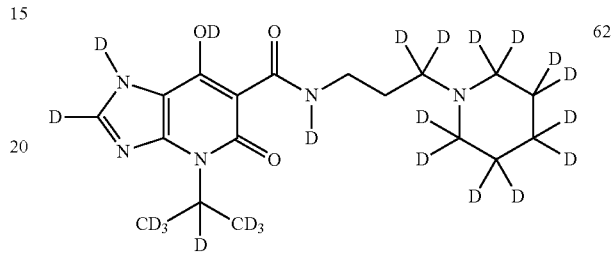
62
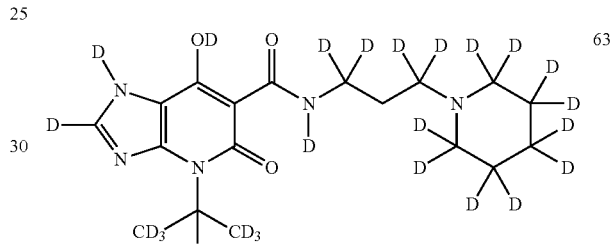
63
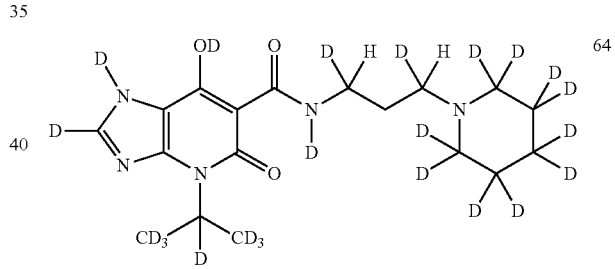
64
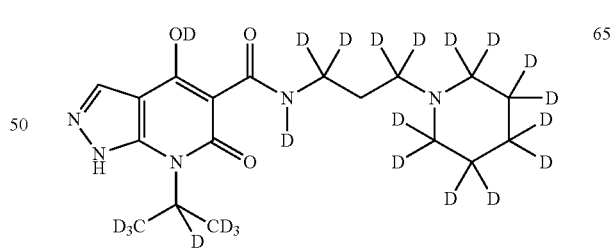
65
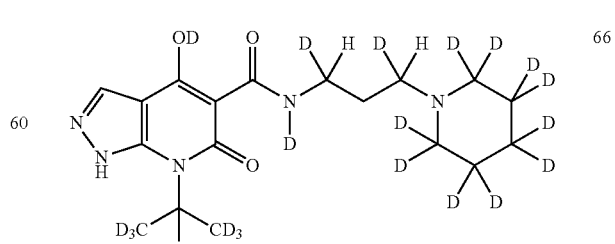
66

TABLE 1-continued

Examples of novel compounds of this invention.

TABLE 1-continued

Examples of novel compounds of this invention.

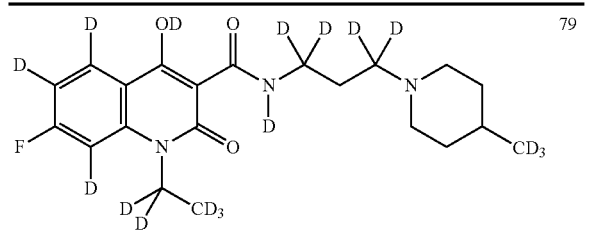
79

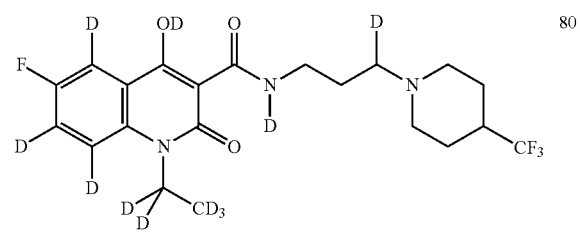
80

Those skilled in the art will recognize or be able to ascertain using no more than routine experimentation, numerous equivalents to the specific reagents can be utilized to produce compounds of the invention. Numerous modifications and variations of the present invention are possible and therefore it is understood that within the scope of the appended claims, the invention may be practiced otherwise that as specifically described herein. Other aspects, advantages and modifications are within the scope of the invention.

What is claimed is:

1. A deuterium enriched compound selected from the group consisting of:

6,7-Dihydro-4-hydroxy-7-isopropyl(d7)-6-oxo-N-(3-(piperidin(d10)-1-yl)propyl)thieno[2,3-b]pyridine-5-carboxamide

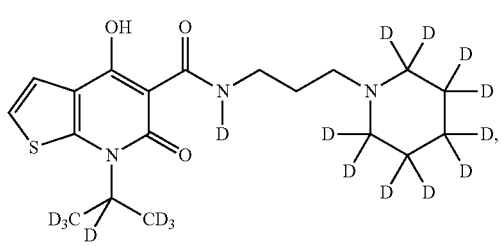

2,3-dideutero-6,7-Dihydro-4-hydroxy-7-isopropyl(d7)-6-oxo-N-(3-(piperidin(d10)-1-yl)prop[r]yl)thien[2,3-b]pyridine-5-carboxamide

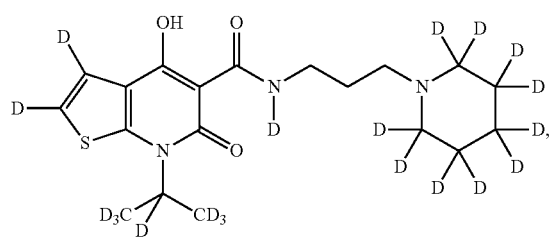

2,3-dideutero-6,7-Dihydro-4-hydroxy-7-isopropyl-6-oxo-N-(3-(piperidin(d10)-1-yl)propyl-d1)thieno[2,3-b]pyridine-5-carboxamide

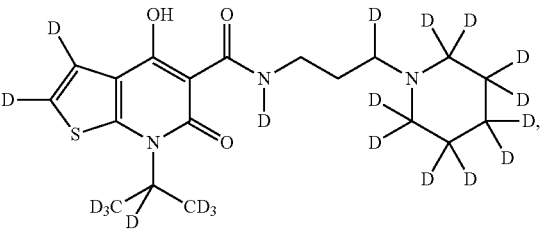

2,3-dideutero-6,7-Dihydro-4-hydroxy-7-isopropyl(d7)-6-oxo-N-(3-(piperidin(d10)-1-yl)propyl-d4)thieno[2,3-b]pyridine-5-carboxamide

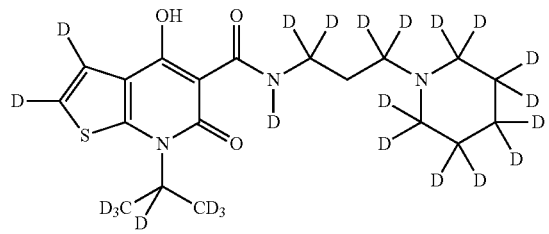

and the pharmaceutically acceptable salts thereof.

2. The compound of claim 1, 6,7-Dihydro-4-hydroxy-7-isopropyl($d_7$)-6-oxo-N-(3-(piperidin($d_{10}$)-1-yl)propyl)thieno[2,3-b]pyridine-5-carboxamide as the potassium salt

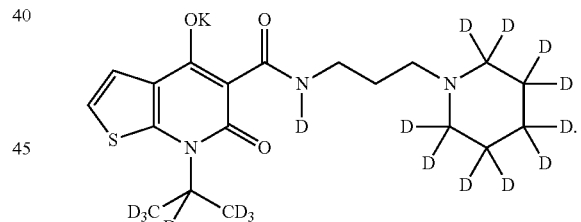

3. The compound of claim 1, 2,3-dideutero-6,7-Dihydro-4-hydroxy-7-isopropyl($d_7$)-6-oxo-N-(3-(piperidin($d_{10}$)-1-yl)prop[r]yl)thien[2,3-b]pyridine-5-carboxamide as the potassium salt thereof.

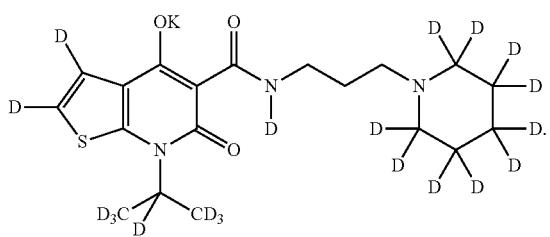

4. The compound of claim 1, 2,3-dideutero-6,7-Dihydro-4-hydroxy-7-isopropyl-6-oxo-N-(3-(piperidin(d10)-1-yl)propyl-d1)thieno[2,3-b]pyridine-5-carboxamide, as the potassium salt thereof
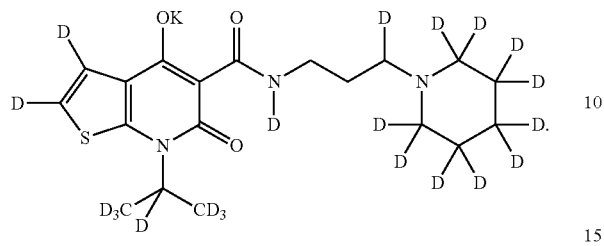
5. The compound of claim 1, 2,3-dideutero-6,7-Dihydro-4-hydroxy-7-isopropyl($d_7$)-6-oxo-N-(3-(piperidin($d_{10}$)-1-yl)propyl-$d_4$)thieno[2,3-b]pyridine-5-carboxamide as the potassium salt thereof
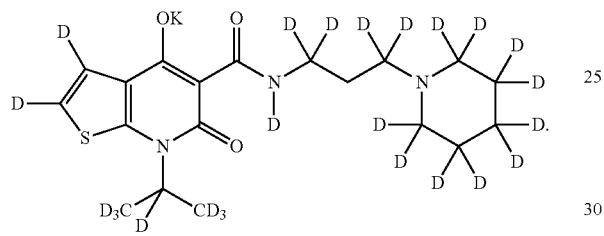
\* \* \* \* \*